United States Patent
Popescu

(10) Patent No.: US 9,927,966 B2
(45) Date of Patent: Mar. 27, 2018

(54) METHOD FOR ENABLING AN INTERACTION BETWEEN AN ASSISTANCE DEVICE AND A MEDICAL APPARATUS AND/OR AN OPERATOR AND/OR A PATIENT, ASSISTANCE DEVICE, ASSISTANCE SYSTEM, UNIT, AND SYSTEM

(71) Applicant: Siemens Aktiengesellschaft, München (DE)

(72) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 462 days.

(21) Appl. No.: 14/640,259

(22) Filed: Mar. 6, 2015

(65) Prior Publication Data
US 2015/0253979 A1  Sep. 10, 2015

(30) Foreign Application Priority Data

Mar. 7, 2014 (DE) ................. 10 2014 204 251

(51) Int. Cl.
  *B25J 9/06* (2006.01)
  *G06F 3/0484* (2013.01)
  (Continued)

(52) U.S. Cl.
  CPC .......... *G06F 3/04847* (2013.01); *A61B 6/46* (2013.01); *A61B 8/46* (2013.01); *G06F 3/011* (2013.01);
  (Continued)

(58) Field of Classification Search
  CPC ...... B25J 9/1689; B25J 9/1656; B25J 13/025; G05B 2219/40131; G05B 2219/39253;
  (Continued)

(56) References Cited

U.S. PATENT DOCUMENTS

2003/0216836 A1  11/2003  Treat et al.
2007/0299559 A1*  12/2007  Janssen ................. B25J 9/1697
  700/259

(Continued)

FOREIGN PATENT DOCUMENTS

JP  2003311669 A  11/2003
JP  2010082714 A  4/2010
(Continued)

OTHER PUBLICATIONS

IBM& "Watson" Computing System to Challenge All Time Greatest Jeopardy! Champions, Dec. 14, 2010 in http://www-03.ibm.com/press/us/en/pressrelease/33233.wss; 2010; Dec. 14, 2010.

(Continued)

*Primary Examiner* — Dalena Tran
(74) *Attorney, Agent, or Firm* — Schiff Hardin LLP

(57) ABSTRACT

In a method for enabling an interaction between an assistance device and a medical apparatus and/or an operator and/or a patient, input information are acquired by an input interface of the assistance device, the input information including information of the medical apparatus and/or of the operator and/or of the patient. The acquired input information is transferred from the input interface to a computer. The input information are processed by the computing unit so as to generate an interaction instruction on the basis of the processed input information. The generated interaction instruction is transferred from the computing unit to an interaction interface of the assistance device and an interaction with an environment of the assistance device is performed on the basis of the interaction instruction via the interaction interface.

27 Claims, 5 Drawing Sheets

(51) Int. Cl.
  *G06F 3/0481* (2013.01)
  *A61B 8/00* (2006.01)
  *G06F 3/01* (2006.01)
  *G06F 3/03* (2006.01)
  *A61B 6/00* (2006.01)
  *G06F 19/00* (2018.01)

(52) U.S. Cl.
  CPC ............ *G06F 3/017* (2013.01); *G06F 3/0304* (2013.01); *G06F 3/0481* (2013.01); *G06F 19/3406* (2013.01); *G06F 19/3418* (2013.01)

(58) Field of Classification Search
  CPC .......... G05B 2219/40122; A01B 34/20; A01B 34/10; A01B 2090/3954
  USPC ....... 700/3, 245, 260, 275; 318/568.11, 566, 318/628
  See application file for complete search history.

(56) References Cited

U.S. PATENT DOCUMENTS

| | | | |
|---|---|---|---|
| 2008/0242952 A1* | 10/2008 | Jung | A61B 5/411 600/300 |
| 2010/0063630 A1* | 3/2010 | Sutherland | A61B 34/70 700/264 |
| 2011/0276058 A1 | 11/2011 | Choi et al. | |
| 2012/0035764 A1 | 2/2012 | Lipow et al. | |
| 2012/0071891 A1* | 3/2012 | Itkowitz | A61B 19/2203 606/130 |
| 2012/0283746 A1 | 11/2012 | Hu et al. | |
| 2013/0218340 A1 | 8/2013 | Hager et al. | |
| 2013/0342350 A1 | 12/2013 | Popescu | |
| 2014/0002624 A1 | 1/2014 | Nemoto et al. | |
| 2015/0073598 A1 | 3/2015 | Rosenstein et al. | |

FOREIGN PATENT DOCUMENTS

WO 2013186794 A2 12/2013
WO WO-2013/186794 A2 12/2013

OTHER PUBLICATIONS

Woollaston, Victoria: "IBM Watson" in http://www.dailymail.co.uk/sciencetech/article-2329080/IBM-reveals-worlds-advanced-set-let-loose-centreoperator.html#ixzz3Qyzn4lhl, May 22, 2013.
Knight, Will: "Baxter the Blue-Collar Robot" Apr. 23, 2013, in MIT Technology Review magazine, May/Jun. 2013; Apr. 23, 2013.
Telepresence Robots.com, VGO ROBOT; 2013.

* cited by examiner

METHOD FOR ENABLING AN INTERACTION BETWEEN AN ASSISTANCE DEVICE AND A MEDICAL APPARATUS AND/OR AN OPERATOR AND/OR A PATIENT, ASSISTANCE DEVICE, ASSISTANCE SYSTEM, UNIT, AND SYSTEM

BACKGROUND OF THE INVENTION

Field of the Invention

The present invention concerns a method for enabling interaction between an assistance device and at least one of a medical apparatus, an operator of the assistance device, and a patient in the environment of the assistance device. The invention also concerns an assistance device that is operable in accordance with such a method, and an assistance system composed of a computer and an assistance device that are operable to implement such a method. The invention also concerns an assembly composed of a computer and multiple assistant devices, for implementing such a method. The invention also concerns a medical system that includes a medical apparatus, a computer and an assistance device for implementing such a method.

Description of the Prior Art

Medical apparatuses are typically employed for the treatment and/or examination of a patient. For example, medical imaging examinations are implemented using medical imaging devices, such as a magnetic resonance apparatus, a computed tomography apparatus, a PET (positron emission tomography apparatus), etc., in the investigation of a variety of medical problems. In such cases the treatment and/or examination of the patient by the medical apparatus are/is typically carried out with the support of operating personnel, for example nursing staff, technical staff, X-ray assistants or physicians.

SUMMARY OF THE INVENTION

An object of the invention is to provide enhanced support for a workflow sequence of a medical examination and/or treatment.

This object is achieved in accordance with the invention by a method for enabling an interaction between an assistance device and an assistance recipient such as a medical apparatus and/or an operator and/or a patient, that includes the following steps.

Input information is entered, via an input interface, to the assistance device, the input information including information of the medical apparatus and/or of the operator and/or of the patient.

The acquired input information is transferred from the input interface to a computer.

The input information is processed by the computer.

An interaction instruction is generated by the computer on the basis of the processed input information.

The generated interaction instruction is transferred from the computer to an interaction interface of the assistance device.

An interaction with an environment of the assistance device is performed on the basis of the interaction instruction via the interaction interface.

The medical apparatus, for example a medical imaging apparatus or a medical treatment apparatus, is situated in an examination room and/or treatment room. The assistance device may also be arranged in the examination room and/or treatment room in this case. Alternatively or in addition, the assistance device may be arranged in a control room of the medical apparatus. The patient can be positioned on a patient support device of the medical apparatus in the examination room and/or treatment room. The assistance device can be physically present in the examination room and/or treatment room, for example in the form of an, in particular mobile, robot.

The assistance device is preferably designed as an autonomous device. Accordingly, the assistance device is embodied independently of, in particular separately from, a medical apparatus. The assistance device is advantageously embodied to execute an autonomous movement and/or autonomous actions. An assistance device can be assigned to a medical apparatus inasmuch as the assistance device has a data interface for the purpose of transferring data to the medical apparatus.

The input information can include optical input information and/or acoustic input information and/or tactile input information. The assistance device can register the input information by means of a suitable sensor of the input interface, for example an optical sensor, an acoustic sensor and/or a contact sensor. The input information can in this case be a communication from the patient and/or the operator, for example a question. Alternatively or in addition, an event, for example an action of the patient and/or of the operator, can be acquired as input information by means of the input interface. The input information can also be an input command. The input interface of the assistance device can also, of course, acquire further input information deemed beneficial by the person skilled in the art.

The input interface is connected to the computer with a view to an exchange of data. The computer can be integrated into the assistance device. Particularly advantageously, the computer is an external computer and is positioned at a spatially remote location from the examination room and/or treatment room. The computer can advantageously incorporate artificial intelligence which is used by the computer when processing the input information and generating the interaction instruction on the basis of the processed input. The computer can accordingly generate an interaction instruction which is tailored to match conditions in the examination room and/or is a question of the operator and/or the patient.

The interaction instruction is in particular an instruction for performing an interaction. The interaction instruction is generated by means of the computer and is advantageously suitably adapted to match the acquired input information. The interaction instruction is furthermore transferred from the computer to the interaction interface of the assistance device. For this purpose the computer and the interaction interface are advantageously connected to one another with a view to an exchange of data. The assistance device performs the interaction in particular with the medical apparatus and/or the operator and/or the patient.

The interaction can be in the form of an output of output information, for example a voice output and/or an optical output. The interaction can also comprise a physical interaction with an environment of the interaction interface.

By means of the proposed approach it is possible to realize an efficient and particularly simple interaction between the assistance device and the patient and/or operator and/or the medical apparatus. An interaction with the patient and/or the operator and/or the medical apparatus can also take place during an examination and/or treatment by means of the medical apparatus.

One embodiment variant provides that the interaction instruction includes output information which is transferred from the computer to an output interface of the interaction interface, the output interface outputting the output information to the medical apparatus and/or the operator and/or the patient.

The output information can include details concerning a planned examination and/or treatment of the patient by means of the medical apparatus. Alternatively or in addition, the output information can include at least information and/or an instruction for the patient and/or the operator. For that purpose the output information can at least partially include optical output information which is projected onto a display surface of the medical apparatus and/or of the patient by means of a projection unit of the output interface. Alternatively or in addition, the output information can also include acoustic output information which is output to the operator and/or patient in particular by means of a loudspeaker of the output interface. Of course, the output interface of the assistance device can also output further output information deemed beneficial by the person skilled in the art.

The assistance device can provide the operator and/or patient with meaningful output information based on the input information. Thus, for example, the assistance device can provide the operator and/or the patient with intelligent information in respect of the treatment and/or examination of the patient that is to be carried out by means of the medical apparatus.

In an embodiment, the interaction instruction includes a gripper arm instruction which is transferred from the computer to a gripper arm of the interaction interface, the assistance device performing a physical interaction with an environment of the gripper arm by means of the gripper arm on the basis of the gripper arm instruction.

The assistance device can actively support the operator by means of the gripper arm. Thus, the assistance device can use the gripper arm to pass the operator implements that are required for preparing the patient for an examination and/or treatment by means of the medical apparatus.

In another embodiment, the interaction instruction includes a locomotion instruction which is transferred from the computer to a locomotion unit of the interaction interface, the assistance device executing a movement by the locomotion unit on the basis of the locomotion instruction.

For this purpose the assistance device can advantageously be embodied at least in part as a robot and the locomotion unit can be a part of the robot. In particular the assistance device can change its relative position with respect to the medical apparatus and/or with respect to the patient and/or with respect to the operator. The locomotion instruction can be generated in particular on the basis of optical input information. The optical input information can in particular comprise information concerning a position of the operator and/or the patient in the room and/or with respect to the medical apparatus.

A change in position of the assistance device is advantageously carried out when the assistance device is located in a field of view of the operator and/or impedes the work of the operator due to its physical presence. A change in position of the assistance device can also be useful during the examination and/or treatment of the patient by means of the medical apparatus. In that case the assistance device can advantageously position itself in the field of view of the patient so that the patient is aware of the presence of the assistance device. Furthermore, the assistance device can change its position by means of the locomotion in such a way that the assistance device assumes an advantageous position for a projection surface for the purpose of projecting optical output information. In addition, the assistance device can change its position by means of the locomotion in such a way that the assistance device assumes an advantageous position for detecting a gesture and/or facial expression and/or movements of the patient and/or of the operator.

In a further embodiment, the interaction instruction includes a movement instruction that is transferred from the computer to a movable subsection of the interaction interface, the movable subsection changing its position with respect to a further subsection of the assistance device on the basis of the movement instruction.

The movable subsection can change its position with respect to a base body of the assistance device, which can be for example a torso of a robot, in particular on the basis of the movement instruction. In this case it is important that the movable subsection is able in particular to change its position relative to a further subsection of the assistance device. If the assistance device moves as a whole by means of the said locomotion unit, the movable subsection can perform an additional movement relative to the further subsection of the assistance device independently of said locomotion.

As a result of the movement of the movable subsection, elements of the assistance device that are arranged on the movable subsection can be brought into an advantageous position, in particular independently of a locomotion of the assistance device as a whole. Thus, for example, a projection unit can be arranged on the movable subsection. The movable subsection can rotate such that the projection unit can assume an advantageous orientation with respect to a projection surface, without a rotation of the entire assistance device being necessary.

In another embodiment, the input information includes a voice input in natural language originating from the operator and/or the patient, the computer employing a natural language processing method for processing the input information.

The term "natural language" typically refers to a language that is spoken by human beings and has evolved over the course of a historical development. Natural languages can also include gestures and/or facial expressions and/or inflection and/or intonation for modulating the communication. In contrast to formal languages, natural languages typically exhibit structural and lexical ambiguities.

A possible way of processing the input information formulated in natural language is to convert the input information formulated in natural language into text by means of a speech-to-text algorithm. The computer can then attribute a meaning to the text for example by means of latent semantic analysis (also known as latent semantic indexing, abbreviated to LSI).

By processing natural language, the assistance device is advantageously able to respond to queries of the patient, the latter typically having no knowledge of structured voice commands for controlling the assistance device. The assistance device is also able to process complicatedly formulated questions and to generate an appropriate interaction instruction in response. Advantageously, the interaction instruction can then include acoustic output information. The output information can likewise be formulated in natural language. The output of acoustic output information formulated in natural language can contribute toward reassuring the patient. In this way a particularly simple and intuitive communication can take place between the assistance device and the patient and/or the operator.

In another embodiment, a gesture and/or facial expression and/or body movement of the patient and/or the operator are/is acquired as input information by means of an optical sensor of the input interface, the interaction instruction being generated on the basis of the captured gesture and/or facial expression and/or body movement.

The optical sensor can be a 3D image data acquisition unit, a 3D camera for example. Accordingly, the assistance device is able in particular to capture a non-verbal communication of the patient and/or of the operator. The non-verbal communication can then be processed by the computer in combination with voice inputs of the patient and/or operator. Advantageously, the assistance device can also recognize an emotional state of the patient on the basis of the gesture and/or facial expression and/or body movement of the patient. The emotional state can then be processed as input information by the computer and an interaction tailored to the emotional state of the patient can be performed, for example an output of a soothing piece of music and/or a calming image, by the output interface of the interaction interface.

The recognition of a gesture and/or facial expression and/or body movement of the patient and/or operator accordingly increases the versatility of the application possibilities of the assistance device. If the assistance device has a locomotion unit, then the assistance device can position itself particularly advantageously in the examination room and/or treatment room in order to recognize the gesture and/or facial expression and/or body movement of the patient and/or of the operator.

In another embodiment, information data relating to an examination and/or treatment of the patient by means of the medical apparatus is stored in at least one database, the interaction instruction being generated on the basis of the information data stored in the at least one database.

The computer can load the information data from the at least one database. The at least one database can for example comprise a medical database containing specialized knowledge in relation to the examination and/or treatment of the patient by means of the medical apparatus. Thus, medical reference books and/or scientific papers can be stored in the at least one database. For example, contraindications relevant to the examination and/or treatment by means of the medical apparatus can be stored in the at least one database and the output information can include information for the operating staff in relation to the contraindications.

The at least one database includes a patient database. The patient database is specific to the individual medical institution, for example the individual hospital, in which the medical apparatus is located. The patient database can therefore be a part of a hospital information system of the medical institution. The information data specific to the patient can include information concerning the state of the patient's health and/or a patient history, for example concerning earlier illnesses of the patient, and/or concerning further planned examinations and/or treatments of the patient and/or concerning patient preferences, for example a certain piece of music during the treatment and/or examination of the patient by means of the medical apparatus.

Accordingly, the interaction instruction can advantageously be tailored specifically to the particular patient that is to be examined and/or treated by means of the medical apparatus. For example, the interaction can include an output of acoustic and/or optical output information personalized to the patient, which is designed to reduce in the patient a possible apprehension regarding the treatment and/or examination by means of the medical apparatus. Such output information can be for example a favorite piece of music of the patient and/or a projected calming image in accordance with the patient's wishes.

In another embodiment, the interaction instruction and the associated input information on the basis of which the interaction instruction was generated are stored as information data in at least one database.

Accordingly, the at least one database can be embodied as a self-learning database. The interaction instruction can be stored together with the associated input information as training data in the at least one database. The quality of the data stored in the at least one database can therefore be improved continuously.

In a further embodiment, in addition to the acquired input information, the computer uses interaction instructions stored in the database and/or stored input information in order to generate the interaction instruction.

In this way, when next accessing the database, the computer can directly retrieve the interaction instruction corresponding to the input information and does not have to determine this afresh first. The quality of the output interaction instructions can therefore be improved continuously.

In another embodiment, during the generation of the interaction instruction, the computer produces a number of hypotheses for potential interaction instructions and evaluates the number of hypotheses for the potential interaction instructions.

The evaluation of the number of hypotheses can be performed by the computer in parallel, for example by means of a number of processors of the computer. In order to generate the number of hypotheses the computer can search in a variety of answer sources, databases for example, for potential interaction instructions based on the processed input information. The number of hypotheses can be filtered prior to the evaluation of the number of hypotheses.

The number of hypotheses for the potential interaction instructions can be evaluated on the basis of the processed input information and/or on the basis of evidence sources, for example additional information data loaded from at least one database. The evaluation of the number of hypotheses can include determining a degree of certainty that the hypothesis for the potential interaction instruction includes an appropriate interaction instruction based on the processed input information.

The computer can subsequently consolidate the number of hypotheses for the potential interaction instructions. The computer can thereupon compare the number of hypotheses on the basis of their evaluations. The generation of the interaction instruction then advantageously includes selecting a potential interaction instruction which belongs to that hypothesis of the number of hypotheses that has the highest rating.

When processing the input information, the computer can therefore draw logical conclusions from the input information, in particular by means of information from the further information source. In this way the computer can automatically determine the significance of the input information during the processing of the input information. Accordingly, a particularly suitable interaction instruction can be generated on the basis of the input information.

In another embodiment, the interaction with the environment of the assistance device is performed together with an output of the associated rating on the basis of at least one of the potential interaction instructions.

In this way the evaluation of the hypothesis of the executed interaction instruction can be output to the operator and/or the patient, in particular acoustically. Alternatively or in addition, information about an answer source used during the generation of the hypothesis, the title of a reference book used for example, can be output. Alternatively or in addition, a reason for the selection of the hypothesis and/or alternative hypotheses can also be output.

Accordingly, additional meta information can be provided to the operator and/or the patient. This can make it easier for and/or enable the operator and/or the patient to make an assessment of the executed interaction. In this case the interaction is advantageously embodied as an output of output information. If, for example, in addition to the output information, the assistance device communicates to the operator and/or the patient that the output information has a high degree of certainty, the operator and/or the patient can possibly have confidence in the output information. Accordingly, the output information of the assistance device can particularly advantageously be combined with the human assessment capacity of the patient and/or the operator.

In another embodiment, the computer is an external computer that is connected to a number of assistance devices assigned to different medical apparatuses with a view to an exchange of data.

Accordingly, a number of assistance devices can access the external computer. The external computer is arranged in particular outside of the examination room and/or treatment room in which the medical apparatus and/or the assistance device are/is located. The external computer can advantageously also be arranged outside of the medical institution, for example outside of the hospital in which the medical apparatus is located. The external computer can therefore be located in a computer center which is connected to different medical institutions. This results in the advantage that an external computer, which is then advantageously embodied as a high-performance computer, can perform computational tasks for a number of assistance devices. This enables a cost saving to be made. Furthermore, because in particular in terms of its placement it is not restricted to the examination room and/or the assistance device, the external computer can also provide a particularly high level of computing power.

The external computer is connected to the assistance device in particular with respect to an, advantageously rapid, exchange of data. The processing of the input information and/or the generation of the interaction instruction on the basis of the processed input information can be carried out on the external computer. For this purpose either the input information can be transferred directly from the input interface of the assistance device to the external computer or the processed input information can be transferred from the computer to the external computer.

The invention furthermore concerns an assistance device for supporting a medical examination process and/or treatment process of a patient. The assistance device has an input interface and an interaction interface and is configured to implement the method according to the invention. Accordingly, the assistance device is configured to implement any or all embodiments of the method for enabling an interaction between the assistance device and a medical apparatus and/or an operator and/or a patient, as described above.

The input interface is designed to acquire input information, the input information including information of the medical apparatus and/or of the operator and/or of the patient. The interaction interface is designed to perform an interaction with an environment of the assistance device on the basis of an interaction instruction.

In an embodiment of the assistance device, the interaction interface has an output interface.

The output interface can include a projection unit. The output interface can additionally include an acoustic output unit, in particular a voice output unit, for emitting acoustic signals to the operator and/or the patient.

Accordingly, the assistance device has a bidirectional communications interface, which is formed by the input interface and the output interface. The bidirectional communications interface is advantageously embodied audio-visually. This enables different types of information to be exchanged between the assistance device and the patient and/or the operator.

In an embodiment of the assistance device, the interaction interface has a gripper arm.

The gripper arm is arranged on the arms. The interaction interface can also have more than one gripper arm. The interaction interface can be an articulated joint unit, which preferably is movable. The articulated joint unit can have multiple of articulated joints, which enable the gripper arm to perform a variety of movements. A force sensor can be arranged on at least one articulated joint of the multiple articulated joints. The force sensor can be connected to a force controller which governs a control of the articulated joints. The interaction interface can also have a contact sensor, which is able to register a contact. The gripper arm affords a great range for an interaction of the interaction interface. The gripper arm can furthermore offer an additional interaction possibility, in particular in addition to the output of optical and/or acoustic output information.

In another embodiment of the assistance device, the interaction interface has a locomotion unit.

The locomotion unit can include locomotion components, rollers for example. The locomotion unit can include a motor for generating a drive torque, the drive torque being transmitted to the locomotion components. If the assistance device is embodied as a humanoid robot for example, then the locomotion unit can also be embodied at least in part as a leg, in particular having movable articulated joints. The locomotion unit is embodied in particular to change a position of the assistance device on a plane of motion in at least two spatial directions. The locomotion unit is embodied particularly for changing the position of the assistance device as a whole.

The assistance device can change its position relative to the medical apparatus and/or to the operator and/or to the patient by operation of the locomotion unit. Accordingly, the assistance device can assume a particularly advantageous position in the room in order, for example, to be able to project a warning message to the right point. An assistance device embodied as a robot can also travel automatically to a charging station for example by operation of the locomotion unit.

In another embodiment of the assistance device, the interaction interface has a movable subsection that is designed to change its position with respect to a further subsection of the assistance device.

Components of the assistance device can be arranged on the movable subsection. For example, at least one component of the output interface and/or a component of the input interface and/or the gripper arm can be arranged on the movable subsection. This component can then execute a movement independently of a locomotion of the assistance device as a whole. Accordingly, the component can assume an advantageous position.

In another embodiment variant of the assistance device, the assistance device has a data interface to an external computer.

The data interface can enable transfer of data between the input interface and the external computer and/or a transfer of data between the external computer and the interaction interface. The external computer can be designed to process the input information. The external computer can be designed to generate an interaction instruction on the basis of the processed input information. The external computer can be connected to multiple assistance devices assigned to different medical apparatuses with a view to exchanging data.

One embodiment of the assistance device provides that the assistance device is embodied at least in part as a robot.

The robot can include the voice recording unit and/or the optical sensor and/or the projection unit and/or the acoustic output unit. The robot advantageously includes the locomotion unit and/or the gripper arm. An assistance device embodied only in part as a robot typically includes further components that are installed independently of the robot, in the examination room and/or treatment room for example. Advantageously, the computer, in particular the external computer, is located independently of the robot. The assistance device can also be designed in its entirety as a robot.

The robot can be designed to interact physically with its environment. Accordingly, the robot, for example, can actively support the operator during the preparation of the patient for the examination and/or treatment by the medical apparatus. For example, the robot can pass the operator instruments required for the examination and/or treatment.

In an embodiment of the assistance device, the robot is designed in the form of a humanoid robot.

A humanoid robot offers the advantage that it can appear familiar to the patient. The humanoid robot can be constantly present in the examination room and/or treatment room. The presence of a humanoid robot in the examination room and/or treatment room, in particular when the operator has left the room, can put the patient at ease. The humanoid robot can also represent an assurance to the patient that the patient has a means of communication at all times.

The invention furthermore concerns an assistance system having a computer and an assistance device according to the invention, the computer being designed to implement the method according to the invention in combination with the assistance device. Accordingly, the assistance system is designed to implement any or all embodiments of the method for enabling an interaction between the assistance device and a medical apparatus and/or an operator and/or a patient, as described above.

The input interface and the computer are designed to transfer the acquired input information from the input interface to the computer. For this purpose, the input interface is connected to the computer for the exchange of data. The computer is designed to process the input information. The computer is designed to generate an interaction instruction on the basis of the processed input information. The computer and the interaction interface are designed to transfer the generated interaction instruction from the computer to the interaction interface. To that end, the computer and the interaction interface are connected to one another for an exchange of data.

In an embodiment of the assistance system, the interaction interface includes an output interface and the computer has an output control module which is embodied for controlling the output interface.

For controlling the output interface, the output control module can transfer output information to the output interface. The output interface can then output the output information. To that end, the output control module is connected to the output interface for an exchange of data.

In another embodiment of the assistance system, the interaction interface includes a gripper arm and the computer has a gripper arm control module designed to control the gripper arm.

For controlling the gripper arm, the gripper arm control module can transfer a gripper arm instruction to the gripper arm. The gripper arm can then perform a physical interaction with the environment on the basis of the gripper arm instruction. To that end, the gripper arm control module is connected to the gripper arm for an exchange of data.

In another embodiment of the assistance system, the interaction interface has a locomotion unit and the computer has a locomotion control module designed to control the locomotion unit.

For controlling the locomotion unit, the locomotion control module can transfer a locomotion instruction to the locomotion unit. The locomotion unit can then change a position of the assistance device in the room on the basis of the locomotion instruction. To that end, the locomotion control module is connected to the locomotion unit for an exchange of data.

In another embodiment of the assistance system, the interaction interface has a movable subsection that is designed to change its position with respect to a further subsection of the assistance device, the computer having a movement control module designed to control the movable subsection.

For controlling the movable subsection, the movement control module can transfer a movement instruction to the movable subsection. The movable subsection can then change its position with respect to a further subsection of the assistance device on the basis of the movement instruction. To that end, the movement control module is connected to the movable subsection for an exchange of data.

In an embodiment of the assistance system, the computer has a voice module designed to process a voice input formulated in natural language and received by a voice recording unit of the input interface.

In this case the voice module can employ a natural language processing algorithm.

In another embodiment of the assistance system, the computer has an image processing module designed to process optical signals received by an optical sensor of the input interface.

To that end, the image processing module is designed to perform pattern recognition in the optical signals. The image processing module, for example, can process a human biomechanical movement such as a gesture and/or facial expression and/or body movement of the patient and/or of the operator. The image processing module can also detect, for example, danger situations in the optical signals, for example an incorrect positioning of the patient.

In another embodiment of the assistance system, the computer is designed as an external computer, formed by a parallel-processing supercomputer and/or a cloud computer.

Accordingly, the external computer is configured as a high-performance computer. The external computer can have multiple processors, which are able, for example, to process a number of hypotheses for the interaction instruction in parallel. Accordingly, the operating speed of the external computer can be increased. Such a computer can also be configured for correctly processing particularly complex input information and for generating the appropriate interaction instruction particularly quickly.

The invention furthermore relates to an assembly of a computer and multiple assistance devices according to the invention, the computer being configured to implement the method according to the invention in combination with an individual device among the multiple assistance devices.

This results in the advantage that the multiple assistance devices according to the invention can access the computer.

The multiple assistance devices can be situated at different locations, in different medical institutions for example. The computer can be embodied as a centralized computing system that can be connected to multiple medical institutions. Accordingly, the computer can perform the processing of the input information and the generation of the interaction instruction for multiple assistance devices. The multiple assistance devices can of course perform interactions with the environment independently of one another.

The invention furthermore relates to a system formed by a medical apparatus and an assistance device according to the invention.

The medical apparatus and the assistance device can be arranged in the same examination room and/or in the same treatment room.

The advantages of the assistance device according to the invention, the assistance system according to the invention, the assembly according to the invention, and the system according to the invention essentially correspond to the advantages of the method according to the invention, as explained in detail above. Features, advantages or alternative embodiments mentioned in this regard are also applicable to the other claimed objects, and vice versa.

DESCRIPTION OF THE PREFERRED EMBODIMENTS

Figure 1:
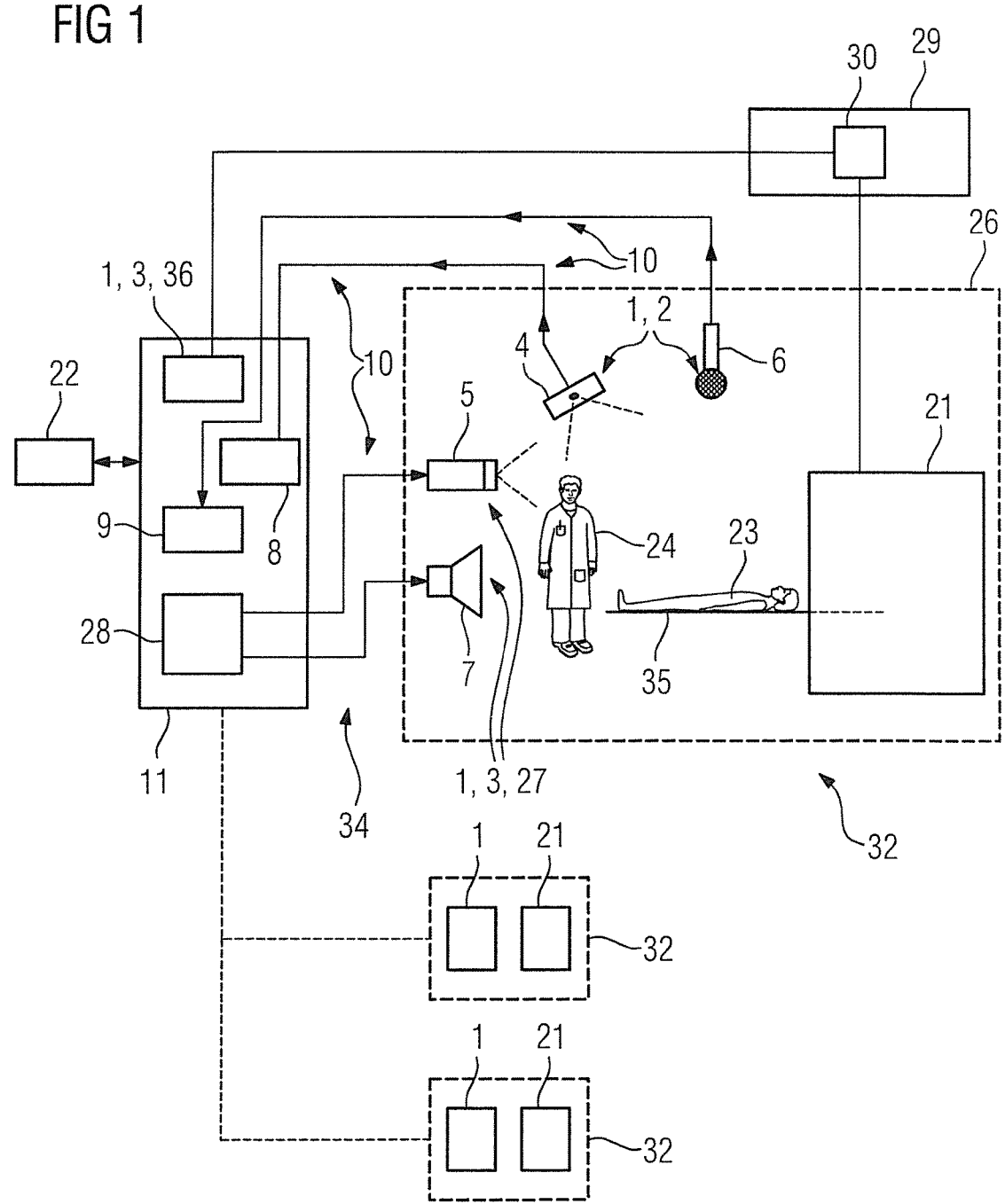
FIG. 1 schematically depicts an assembly according to the invention, formed by multiple systems according to the invention.

FIG. 1 is a schematic illustration of an assembly according to the invention, composed of multiple systems according to the invention. The assembly according to the invention has a computer 11 and multiple systems 32. Each of the multiple systems 32 includes an assistance device 1 and a medical apparatus 21. The computer 11 is designed to implement the method according to the invention in combination with an individual device among the multiple assistance devices 1. The computer 11 in combination with an assistance device 1 forms an assistance system 34 according to the invention.

One of the multiple systems 32 is illustrated in greater detail, while the other systems 32 are indicated merely schematically. Each of the systems 32 according to the invention has a medical apparatus 21 and an assistance device 1 according to the invention. The system 32 illustrated in greater detail comprises an assistance device 1 according to a first embodiment.

In the case shown, the medical apparatus 21 is a medical imaging apparatus 21. The medical imaging apparatus 21 is for example a magnetic resonance apparatus, a single-photon emission tomography apparatus (SPECT apparatus), a positron emission tomography apparatus (PET apparatus), a computed tomography apparatus, an ultrasound apparatus, an X-ray apparatus, or an X-ray apparatus embodied as a C-arm apparatus. The medical imaging apparatus 21 can also be a combined medical imaging apparatus comprising an arbitrary combination of more than one of the cited imaging modalities.

It goes without saying that other medical apparatuses, not shown in FIG. 1, which are not medical imaging apparatuses 21, are also conceivable. In particular the medical apparatus can be a treatment apparatus. Thus, the medical apparatus can alternatively be designed as an apparatus for intensive medicine, for example as a mobile monitoring apparatus and/or respiratory apparatus and/or infusion apparatus and/or dialysis apparatus. Furthermore, the medical apparatus can alternatively be designed as a radiotherapy apparatus. Alternatively, the medical apparatus can be designed as a lithotripsy apparatus. Alternatively, the medical apparatus can also be embodied as a cardiological diagnostic apparatus, for example as an ECG apparatus. It is also conceivable that the medical apparatus is an interventional treatment apparatus for performing an interventional procedure. Of course, other medical apparatuses deemed beneficial by those skilled in the art are also conceivable.

The illustrated medical imaging apparatus 21 has a patient support device on which a patient 23 is positioned. The medical imaging apparatus 21 is controlled by an operator 24. The medical imaging apparatus 21 and the assistance device 1 are located in an examination room 26. Also shown is a control room 29 in which a control unit 30 is arranged for the purpose of controlling the medical imaging apparatus 21.

The assistance device 1 is assigned to the medical imaging apparatus 21. In the case shown the assistance device 1 is also arranged in the examination room 26. According to the present embodiment variant the assistance device 1 is embodied for an, in particular bidirectional, communication with the operator 24 and/or the patient 23 that is to be examined by means of the medical imaging apparatus 21.

For this purpose the assistance device 1 has an input interface 2 that is designed to acquire (receive) input information. The input information can in this case originate, for example, from the operator 24 and/or from the patient 23. In the case shown the input interface 2 has a voice recording unit 6 that is formed, as an example, by a microphone. In addition the input interface 2 has an optical sensor 4, which is formed as an example by a 3D image data acquisition unit.

Obviously, the input interface 2 can also have only one optical sensor 4 and/or only one voice recording unit 6. The input interface can also have multiple optical sensors 4 and/or multiple voice recording units 6. It is conceivable, for example, for the input interface 2 to have an array composed of multiple cameras and/or microphones in order to enable optical and/or acoustic input information to be acquired in an optimal manner from a large part of the examination room 26.

The assistance device 1 comprises an interaction interface 3. In the case shown the interaction interface 3 is designed as an output interface 27 in order to emit output information to the operator 24 and/or the patient 23. In the case shown the output interface 27 has a projection unit 5 formed by a projector. In addition the output interface 27 in the case shown has a voice output unit 7, formed by a loudspeaker.

Obviously the output interface 27 can have only one projection unit 5 and/or only one voice output unit 7. The output interface 27 can also have multiple projection units 5 and/or multiple voice output units 7. It is conceivable, for example, for the output interface 27 to have an array composed of multiple projectors and/or loudspeakers in order to enable optical and/or acoustic output information to be emitted in an optimal manner in a large part of the examination room 26.

In addition, the computer 11 has an apparatus communications interface 36. In the case shown, the apparatus communications interface 36 is a part of the interaction interface 3 of the assistance device 1. The apparatus communications interface 36 is connected to the control unit 30 of the medical imaging apparatus 21 for an exchange of data. As an interaction between the assistance device 1 and the medical imaging apparatus 21, the apparatus communications interface 36 can transfer a command to the control unit 30. The control unit 30 can then control the medical imaging apparatus 21 on the basis of the command. The command can be, for example, an abort command for prematurely terminating an examination of the patient 23 by means of the medical imaging apparatus 21.

The assistance device 1 additionally has a computer 11. In the case shown the computer 11 is designed, as an example, as an external computer 11. Accordingly, the computer 11 is arranged outside of the examination room 26. The computer 11 is also arranged outside of the control room 29. The computer 11 is connected to the plurality of systems 32 with a view to an exchange of data. The computer 11 is arranged spatially separated from the multiple systems 32.

In the case shown the computer 11 is formed by a parallel-processing supercomputer and/or a cloud computer. In the case shown the computer 11 is connected to a database 22. The computer 11 is embodied for retrieving data from the database 22 and/or for storing training data in the database 22.

In an alternative embodiment of the invention the computer 11 can also be designed only in part as an external computer 11. The computer 11 can also be arranged in its entirety in the spatial environment of the assistance device 1, for example in the examination room 26 and/or in a control room assigned to the medical apparatus 21. It is conceivable in this case for example that computing operations are allocated for execution to an external computer 11 and to a computer 11 assigned to the medical apparatus 21 and/or to the assistance device 1.

In the present exemplary embodiment the assistance device 1 has a single computer 11 for processing the input information acquired by means of the input interface 2 and for generating the interaction instruction. In principle it is also conceivable, however, that the assistance device 23 has multiple computers 11 that are responsible separately for example for processing the input information and generating the interaction instruction.

The assistance device 1 has a data interface 10 to the computer 11. In the case shown the data interface 10 has multiple data transfer units. At least some of the data transfer units can be embodied as wireless. The data interface 10 accordingly connects the input interface 2 to the computer 11 for the transfer of data from the input interface 2 to the computer 11. In addition the data interface 10 connects the output interface 27 to the computer 11 for the transfer of data from the computer 11 to the output interface.

The computer 11 has an image processing module 8 designed to process optical signals received by the optical sensor 4. In addition, the image processing module 8 can be designed to generate optical output information for the projection unit 5. To that end, the image processing module 8 is connected via the data interface 10 to the optical sensor 4 and/or to the projection unit 5 for the transfer of data.

The computer 11 additionally has a voice module 9 designed to process a voice input formulated in natural language and received by the voice recording unit 6. The voice module 9 can additionally generate, for example, an acoustic voice output for the voice output unit 7. To that end the voice module is connected to the voice recording unit 6 and/or to the voice output unit 7 for the transfer of data by means of the data interface 10.

The computer 11 additionally has an output control module 28 designed to control the output interface 27. To that end the output interface 27 is likewise connected to the output control module 28 via the data interface 10.

Figure 2:
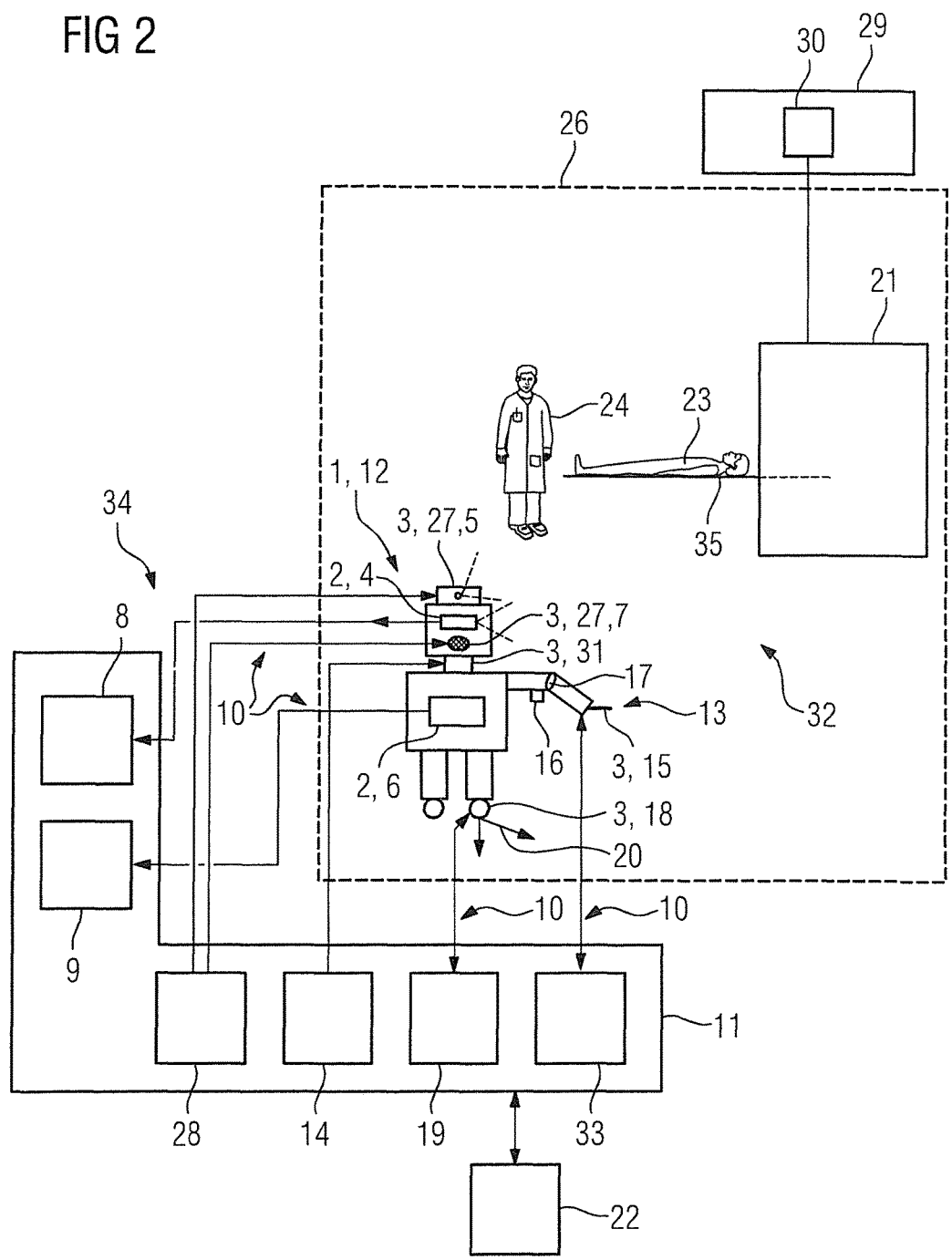
FIG. 2 schematically depicts an assistance system according to the invention.

FIG. 2 is a schematic illustration of an assistance system 34 according to the invention. The assistance system 34 has an inventive assistance device 1, embodied as a robot 12, according to a second embodiment. The assistance system 34 additionally includes a computer 11. Also shown is a medical apparatus 21 which in combination with the assistance device 1 forms a system 32 according to the invention.

The following description is restricted essentially to the differences compared to the exemplary embodiment in FIG. 1, reference being made to the description of the exemplary embodiment in FIG. 1 with respect to like components, features and functions. Substantially like components, features and functions are consistently labeled with the same reference numerals.

In the present example the robot 12 is embodied in the form of a humanoid robot. Accordingly, the robot 12 has a human-like form. In the case shown the humanoid robot 12 has a head, a torso, arms and legs. An alternative embodiment of the robot 12 deemed beneficial by the person skilled in the art is, of course, also conceivable.

In the case shown, all of the elements of the assistance device 1 depicted in FIG. 1 and explained are arranged on the robot 12. Thus, the robot 12 includes the input interface 2 with the optical sensor 4 and the projection unit 5. The optical sensor 4 is advantageously arranged on the head part of the robot 12. The robot 12 includes the interaction interface 3, which includes the output interface 27. The projection unit 5 of the output interface 27 is for example a pico projector which is arranged above the head part. The voice output unit 7 of the output interface 27 is advantageously likewise arranged on the head part of the robot 12. The voice recording unit 6 can be arranged at any desired point on the robot 12.

Obviously, the robot 12 can also have only individual elements of the assistance device 1. Accordingly, the assistance device may be embodied only in part as a robot 12. Thus, for example, the voice recording unit 6 may not be arranged on the robot 12, but can be embodied as a microphone array in the examination room 26.

Also, the robot 12 advantageously does not include the computer 11, but is simply connected to the latter via the data interface 10. As shown in FIG. 1, in FIG. 2 also the input interface 2 and the interaction interface 3 of the robot 12 are connected to the computer 11, for example the image processing module 8 and the voice module 9, via the data interface 10.

In addition the interaction interface 3 of the robot has a gripper arm 15. The gripper arm 15 is designed to engage in a physical interaction with an environment of the assistance device 1. Accordingly, the computer 11 has a gripper arm control module 33 designed to control the gripper arm 15. To that end the gripper arm 15 is likewise connected to the gripper arm control module 33 via the data interface 10.

In the case shown the gripper arm 15 is arranged on an arm of the humanoid robot 12. By means of the gripper arm 15, the assistance device 1, for example, can hand the operator 24 instruments required for preparing the patient 23 for an examination by means of the medical imaging apparatus 21. The interaction interface 13 additionally has an articulated joint unit 17 having a force sensor 16. The articulated joint unit 17 is designed to be movable, the force sensor 16 being able to measure forces acting on the articulated joints of the articulated joint unit 17. The articulated joint unit 17 enables the position of the gripper arm 15 to be changed.

The interaction interface 3 additionally has a locomotion unit 18. The locomotion unit 18 is designed to change the position of the robot 12 in the room. The locomotion unit 18 is designed to change the position of the robot 12 as a whole. Accordingly, the computer 11 has a locomotion control module 19 designed to control the locomotion unit 18. To that end the locomotion unit 18 is likewise connected to the locomotion control module 19 via the data interface 10.

In the case shown, the locomotion unit 18 has rollers as an example. The rollers enable the position of the robot 12 to be changed on a plane of motion 20. In the present case the plane of motion 20 is the floor of the examination room 26. The rollers enable the position of the robot 12 to be changed in at least two spatial directions, in particular on the plane of motion 20. By means of the rollers the robot 12 is able to change its position with respect to the operator 24 and/or with respect to the patient 23 and/or with respect to the medical apparatus 21.

The interaction interface 3 additionally includes a movable subsection 31 designed to change its position with respect to a further subsection of the assistance device. Accordingly, the computer 11 has a movement control module 14 designed to control the movable subsection 31. To that end the movable subsection 31 is likewise connected to the movement control module 14 via the data interface 10.

In the case shown the movable subsection 31 is designed as an example as a rotary articulated joint. The movable subsection is arranged between a head and a torso of the humanoid robot 12. Accordingly, the head of the robot 12 is able to execute a rotary movement independently of the torso of the robot 12. Accordingly, the head of the robot can turn in a suitable direction by a movement of the movable subsection in order, for example, to project optical output information onto a display surface by means of the projection unit 5. The movable subsection can, of course, be designed differently and/or can be arranged differently.

Figure 3:
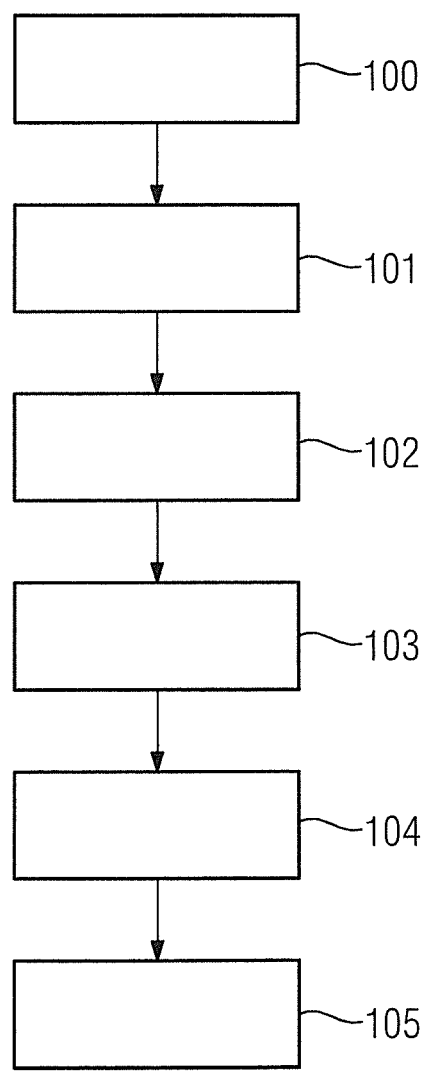
FIG. 3 is a flowchart of a first embodiment of a method according to the invention.

FIG. 3 shows a flowchart of a first embodiment of the method according to the invention for enabling an interaction between an assistance device 1 and a medical apparatus 21 and/or an operator 24 and/or a patient 23.

In a first method step 100, input information is acquired by an input interface 2 of the assistance device 1, the input information including information of the medical apparatus 21 and/or of the operator 24 and/or of the patient 23.

Figure 4:
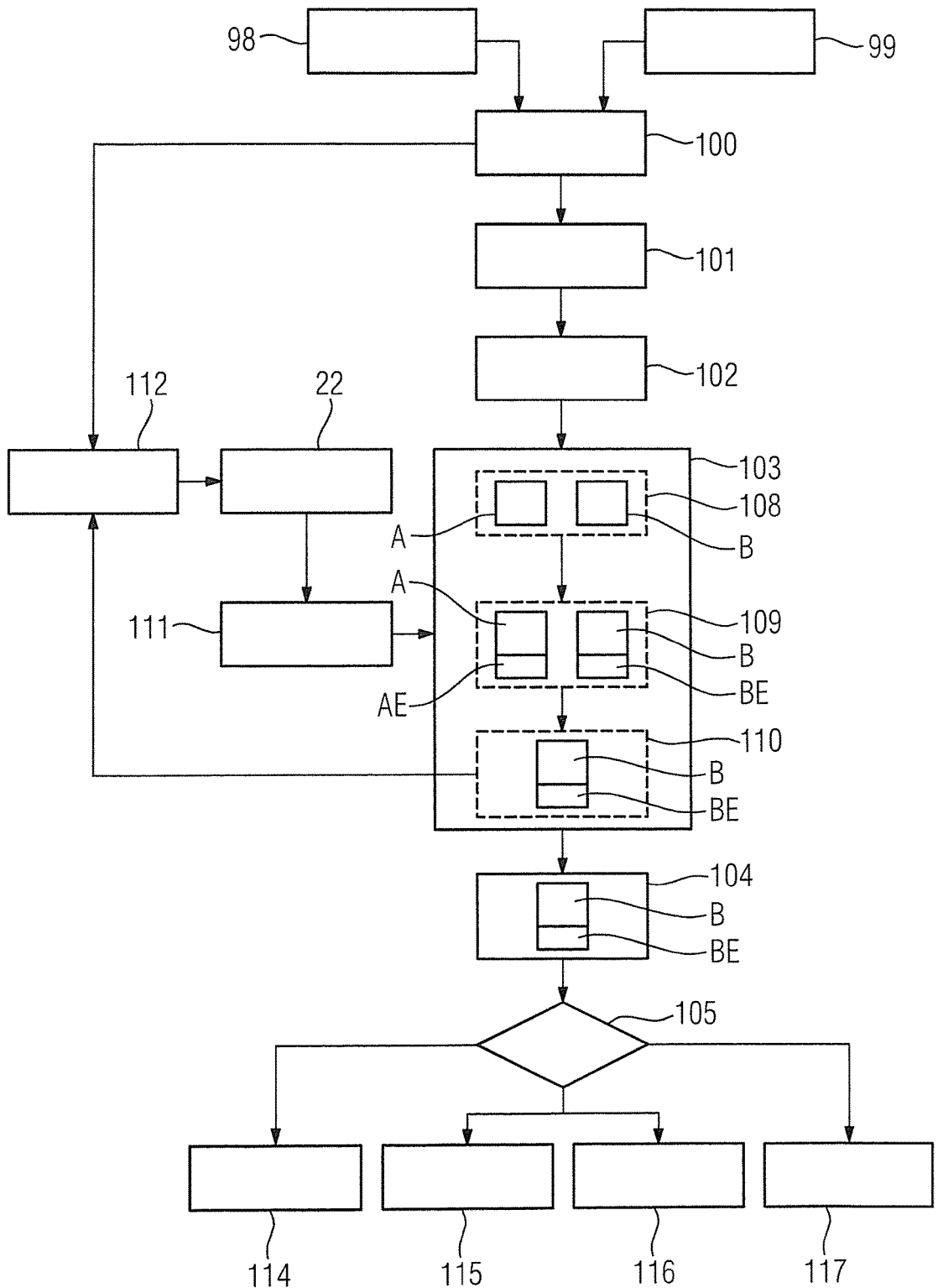
FIG. 4 is a flowchart of a second embodiment of a method according to the invention.

In a further method step 101, the acquired input information is transferred from the input interface 2 to a computer 11. The acquired input information is transferred by a data interface 10 between the input interface 2 and the computer 11. The computer 11 has an external computer 11. The external computer 11 is connected to multiple assistance devices 1, which are assigned to different medical apparatuses 21, in particular for the exchange of data. All of the method steps shown in FIG. 3 and FIG. 4 are therefore performed by the computer 11 and/or the external computer 11.

In a further method step 102, the input information is processed by the computer 11.

In a further method step 103, an interaction instruction is generated on the basis of the processed input information by the computer 11.

In a further method step 104, the generated interaction instruction is transferred from the computer 11 to an interaction interface 3 of the assistance device 1. The transfer of the generated interaction instruction is again effected by means of a data interface 10 between the computer 11 and the interaction interface 3.

In a further method step 105, an interaction with an environment of the assistance device 1 is performed on the basis of the interaction instruction by means of the interaction interface 3.

FIG. 4 shows a flowchart of a second embodiment of the method according to the invention. The following description restricts itself essentially to the differences compared to the exemplary embodiment in FIG. 3, reference being made to the description of the exemplary embodiment in FIG. 3 with respect to like method steps. Substantially like method steps are labeled consistently with the same reference numerals.

The second embodiment of the method according to the invention shown in FIG. 4 essentially includes the method steps 100,101,102,103,104,105 of the first embodiment of the method according to the invention shown in FIG. 3. In addition the second embodiment variant of the method according to the invention shown in FIG. 4 includes additional method steps and substeps. An alternative method sequence to FIG. 4 having only some of the additional method steps and/or substeps shown in FIG. 4 is also conceivable. Obviously, an alternative method sequence to FIG. 4 can also include additional method steps and/or substeps.

In the exemplary embodiment shown in FIG. 4, acoustic input information is provided in a further method step 98. The acoustic input information can be, for example, a voice input by the operator 24 and/or the patient 23 which is formulated in natural language. The voice input is acquired in the further method step 100 by the voice recording unit 6 of the input interface 2. In the further method step 101, the voice input is then processed by the computer 11, in particular a voice module 9 of the computer 11, by means of a natural language processing method.

In the exemplary embodiment shown in FIG. 4, optical input information is additionally provided in a further method step 99. By way of example the operator 24 and/or the patient make/makes a gesture and/or facial expression and/or body movement. The gesture and/or facial expression and/or body movement are/is acquired as input information by an optical sensor 4 of the input interface 2 in the further method step 100. The gesture and/or facial expression and/or body movement are/is processed in the further method step 102 by means of the computer 11, in particular an image processing module 8 of the computer 11. The interaction instruction is then generated by means of the computer 11 in the further method step 103 on the basis of the acquired gesture and/or facial expression and/or body movement.

The non-verbal communication, that is to say the gesture and/or facial expression and/or body movement, can then be processed by the computer 11 in combination with the voice input of the patient and/or operator.

In order to generate the interaction instruction in the further method step 103, the computer 11 is additionally connected to a database 22. The database 22 includes a patient database as an example. Information data relating to an examination and/or treatment of the patient 23 by operation of the medical apparatus 21 is stored in the database 22.

The information data is at least partly specific to the patient 23. In order to generate the interaction instruction, the information data is loaded from the database 22 by means of the computer 11 in a further method step 111. The interaction instruction is then generated in the further method step 103 on the basis of the information data loaded from the database 22.

While the interaction instruction is being generated in the further method step 103, the computer 11 produces a number of hypotheses A, B for potential interaction instructions in a further method step 108. In the case shown in FIG. 4, the computer 11 generates, for example, two hypotheses A, B, namely a first hypothesis A for a first potential interaction instruction, and a second hypothesis B for a second potential interaction instruction. The computer 11 can, of course, also generate a different number of hypotheses A, B.

While the interaction instruction is being generated in the further method step 103, the computer 11 evaluates the multiple hypotheses A, B for the potential interaction instructions in a further method step 109. In the case shown the first hypothesis A is evaluated with a first rating AE, and the second hypothesis B with a second rating BE. The rating BE is in this case by way of example higher than the rating AE.

During the generation of the interaction instruction in the further method step 103, the computer 11 selects the hypothesis B with the highest rating BE in a further method step 110. The assistance device 1 subsequently performs an interaction on the basis of the selected interaction instruction. To that end, the interaction instruction is transferred together with the rating BE of the associated hypothesis B from the computer 11 to the interaction interface 3 in the further method step 104. In the further method step 105, an interaction is performed by means of the interaction interface 3 on the basis of the selected interaction instruction. While the interaction is being performed, the rating BE determined during the evaluation of the multiple hypotheses for that hypothesis B which is assigned to the interaction instruction is also emitted by the output interface 3 in the further method step 105.

In a further method step 112, the interaction instruction and the associated input information on the basis of which the interaction instruction was generated are stored as information data in the database 22. In an application case succeeding in time, the computer 11 can use interaction instructions stored in the database 22 and/or stored input information in addition to the acquired input information for the purpose of generating the interaction instruction.

In the further method step 105, an interaction with an environment of the assistance device 1 is performed by means of the interaction interface 3 on the basis of the interaction instruction. A different module of the interaction interface 3 performs the interaction in this case, depending on the type of the interaction instruction.

If the interaction instruction includes output information that has been transferred from the computer 11 to an output interface 27 of the interaction interface 3, an output interface 27 of the interaction interface 3 emits the output information to the medical apparatus 21 and/or the operator 24 and/or the patient 23 in a further method step 114.

If the interaction instruction includes a gripper arm instruction which has been transferred from the computer 11 to a gripper arm 15 of the interaction interface 3, the assistance device 1 performs a physical interaction with an environment of the gripper arm 15 by the gripper arm 15 on the basis of the gripper arm instruction in a further method step 115.

If the interaction instruction includes a locomotion instruction which has been transferred from the computer 11 to a locomotion unit 18 of the interaction interface 3, the assistance device 1 executes a movement by the locomotion unit 18 on the basis of the locomotion instruction in a further method step 116.

If the interaction instruction includes a movement instruction which has been transferred from the computer 11 to a movable subsection 31 of the interaction interface 3, the movable subsection 31 changes its position with respect to a further subsection of the assistance device 1 on the basis of the movement instruction in a further method step 117. Accordingly, a projection unit 5 which is arranged on the movable subsection 31, for example, can advantageously be aligned.

On the basis of the input information processed in the further method step 102, an action instruction is generated by means of the computer 11, in particular an interaction control module 14 of the computer 11, in a further method step 116. The action instruction is transferred from the computer 11 to an interaction interface 13 of the assistance device 1, the interaction interface 13 performing an interaction with an environment of the interaction interface 13 on the basis of the action instruction.

In addition, in a further method step 117, a locomotion instruction is generated by the computer 11, in particular a locomotion control module 19 of the computer 11, on the basis of the input information processed in the further method step 102. The locomotion instruction is transferred from the computer 11 to a locomotion unit 18 of the assistance device 1, the assistance device 1 executing a movement on a plane of motion 20 by the locomotion unit 18 on the basis of the locomotion instruction.

The method steps of the method according to the invention shown in FIG. 3 and FIG. 4 are performed by the assistance device 1 in combination with the computer 11. For this purpose, the computer 11 includes necessary software and/or computer programs which are stored in a memory unit of the computer 11. The software and/or computer programs include program means which are configured to perform the method according to the invention when the computer program and/or the software in the computer 11 are/is executed by means of the computer 11.

Figure 5:
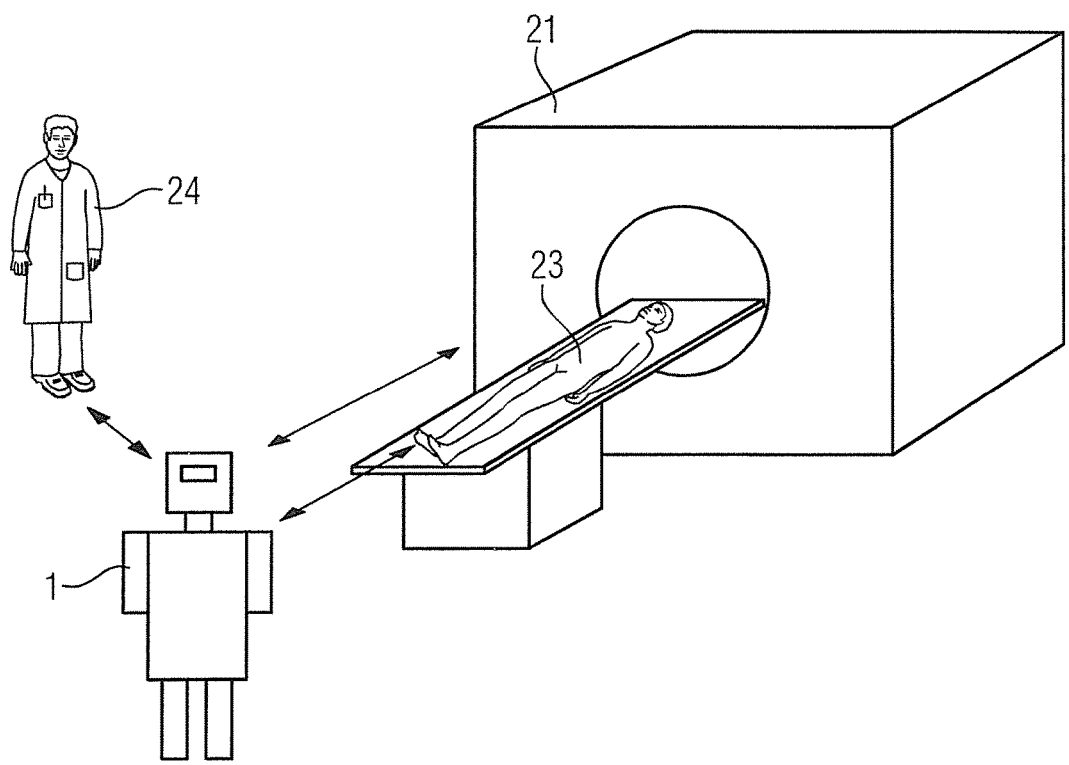
FIG. 5 schematically depicts interaction possibilities of an assistance device in accordance with the invention.

FIG. 5 schematically shows interaction possibilities of an assistance device 1. In particular possible interactions between the assistance device 1 and a patient 23 and/or an operator 24 and/or a medical apparatus 21 are presented hereinbelow. Accordingly, several exemplary application cases of the assistance device 1 are described in the following sections. It goes without saying that further application cases deemed beneficial by the person skilled in the art are also conceivable for the assistance device 1. The assistance device 1 is in this case indicated only schematically. It can assume any desired embodiment deemed beneficial or necessary for the application in question. The assistance device 1 can be designed, for example, as described in FIG. 1 or FIG. 2.

For example, the assistance device 1 can acquire optical signals from objects arranged on a patient support device 35 of the medical apparatus 21 and/or from an arrangement of the patient 23 as input information by means of the input interface 2, which includes for example an optical sensor 4. Accordingly, the assistance device 1 can advantageously monitor the patient 23 with regard to the latter's position and/or with regard to undesirable movements during the examination and/or treatment by the medical apparatus.

The assistance device 1 can then be designed, for example, to provide support in preparing a patient 23 for the treatment and/or examination by means of the medical apparatus 21. The interaction can include an output of output information to the operator 24 by an output interface 27 of an interaction interface 3. By means of such output information the attention of clinical staff overseeing the medical imaging examination, in particular the operator 24, can be quickly drawn to a possible source of error during a preparation and/or positioning of the patient 23 on the patient support device 35, so that in this way an immediate error correction can be carried out by the operator 24 and consequently a particularly time-saving and safe preparation and/or positioning of the patient 23 can be achieved.

In order to provide support during a preparation of the patient 23, the assistance device 1 is advantageously embodied at least in part as a robot 12 and the interaction interface 3 is a part of the robot 12. It is conceivable as a physical interaction that the assistance device 1 passes the operator instruments required for the examination and/or treatment of the patient 23 by the medical apparatus 21, for example fixing devices and/or movable coils for a magnetic resonance examination. For that purpose the interaction interface 3 can include a gripper arm 15. The assistance device 1 can determine the right time for passing the instruments on the basis of the acquired and processed input information. For example, the assistance device 1 can pass the instruments to the operator 24 only when the assistance device 1 has detected by an optical input interface that the patient 23 is positioned on the patient support device 35 of the medical apparatus 21.

In addition the assistance device 1 can be designed, for example, for monitoring an examination and/or treatment of the patient 23 by means of the medical apparatus 21. The assistance device 1 can react particularly rapidly to a registered undesirable movement of the patient 23 during the examination and/or treatment by means of the medical apparatus 21. Restless patients 23 also can be alerted by means of the assistance device to remain motionless during the examination and/or treatment, without any need on the part of the operator 24 in this case to enter the examination room and/or treatment room. In this case the interaction can entail issuing at least one safety warning and/or an instruction to the patient 23 and/or the operator 24 by means of the output interface 27. Thus, an appropriate safety warning can be generated immediately by the assistance device 1 upon detecting a hazardous situation for the patient 23 and/or the operator 24 and output as output information.

In addition the assistance device can, for example, respond to and/or answer questions by the patient 23 during the examination and/or treatment, in particular when the operator 24 is not present in the examination room 26 and/or treatment room. The assistance device 1 can accordingly also contribute to putting the patient 23 at ease during the examination and/or treatment, in particular when it is physically present, for example in the form of the robot 12, in the examination room 26 and/or treatment room during the examination and/or treatment of the patient 23. Accordingly, the above-described interaction between the assistance device 1 and the patient 23 is particularly advantageously embodied as a communication between the assistance device 1 and the patient 23.

Alternatively or in addition, the assistance device 1 can interact with the medical apparatus 21. To that end, an exchange of data between the assistance device 1 and the medical apparatus 21 can take place as the interaction. It is conceivable in this case that the assistance device 1 can send control information to the medical apparatus 21 as a function of the input information. The control information can effect a change of settings, for example of imaging parameters, of the medical apparatus 21. The assistance device 1 can possibly also initiate an emergency shutdown of the medical apparatus 21 and/or a premature termination of the examination and/or treatment by the medical apparatus 21, in particular if a hazardous situation has been detected by the input interface 2.

The interaction can advantageously take place also between the operator 24 and the assistance device 1 during an interventional procedure by means of the medical apparatus 21. The interventional procedure can be for example a biopsy, a catheter examination, a catheter ablation, an angioplasty, an implantation of a stent, or a chemoembolization of a tumor. The proposed interaction between the operator 24 and the assistance device 1 is particularly advantageous especially in the case of interventional procedures, since typically only a limited timeframe is available during an interventional procedure.

During the interventional procedure the assistance device 1 can for example provide valuable information concerning the condition of the patient 23 and/or concerning the intervention that is to be performed. The assistance device 1 can also provide safety alerts during the interventional procedure. The information or alerts can be provided optically or acoustically by the assistance device 1. At the same time the assistance device 1 is able to respond particularly quickly to questions of the operator. In addition, the assistance device 1, in particular an assistance device 1 embodied as a robot 12 and having a gripper arm 15, can also support the interventional procedure to the effect that, for example, the assistance device 1 passes instruments to the operator 24.

In addition the assistance device 1 can for example support a maintenance of the medical apparatus 21 by the operator 24. In such a case the operator 24 is in particular a maintenance operative 24 and/or service operative 24. The support for the maintenance of the medical apparatus 21 by the assistance device 1 can be provided in particular in the case of a service callout and/or at the time of the installation of the medical apparatus 21. The support for the maintenance of the medical apparatus 21 by the assistance device 1 can be provided in particular in addition to the support provided during an examination and/or treatment of the patient 23 by the assistance device 1.

Input information for the assistance device 1 used during a maintenance of the medical apparatus can for example be optical input information concerning a presence of the maintenance operative 24 and/or information data concerning a planned maintenance of the medical apparatus 21 and/or information data concerning measurements performed in the past by the medical apparatus 21 and/or information data concerning problems of the medical apparatus 21 that have occurred in the past.

Advantageously, the assistance device 1 can support the maintenance operative 24 by means of output information concerning a maintenance of the medical apparatus 21 that is to be carried out. The assistance device 1 can also alert the maintenance operative 24 to problems of the medical apparatus 21 that have occurred in the past. Particularly advantageously, the assistance device 1 can alert the maintenance operative 24, by a projected image for example, to danger zones in the maintenance of the medical apparatus 21. Advantageously, the assistance device 1 can also actively support the maintenance operative 24 by the interaction interface 3, in particular a gripper arm 15, to the effect that for example the assistance device 1 passes a tool necessary for the maintenance to the maintenance operative 24. The support for the maintenance of the medical apparatus 21 is accordingly a particularly advantageous further field of application of the assistance device 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for enabling interaction between an assistance device and an assistance recipient, said assistance recipient being selected from the group consisting of a medical apparatus, an operator of a medical apparatus, and a patient receiving treatment or an examination from a medical apparatus, said method comprising:
   acquiring input information via an input interface of an assistance device, said assistance device being configured to execute a plurality of interactions involving said assistance recipient, each interaction providing assistance in a medical procedure, and said input information originating from said assistance recipient;
   transferring the acquired input information from the input interface to a computer;
   in said computer, automatically processing said input information to generate an interaction instruction dependent on said input information;
   transferring the generated interaction instruction from the computer to an interaction interface of said assistance device;
   in said assistance device, identifying, from said interaction instruction, at least one interaction among said plurality of interactions and, via said interaction interface, performing said at least one interaction with said assistance recipient in said environment of said assistance device;
   in at least one database that is accessible by said computer, storing stored data describing at least one of an examination of said patient conducted using said medical apparatus and a treatment of said patient conducted using said medical apparatus; and
   in said computer, accessing said stored data from said at least one database and processing said input information to generate said interaction instruction dependent on the accessed stored data.

2. A method as claimed in claim 1 wherein said interaction interface of said assistance device comprises an output interface, and wherein said method comprises, in said computer, generating output information as a part of said interaction instruction and transferring said output information to said output interface, and, via said output interface, emitting said output information to said assistance recipient.

3. A method as claimed in claim 1 wherein said interaction interface of said assistance device comprises a gripper arm, and wherein said method comprises, in said computer, generating said interaction instruction to include a gripper arm operating instruction, and transferring said gripper arm operating instruction to said interaction interface and, via said gripper arm performing a physical interaction, dependent on said gripper arm operating instruction, with said assistance recipient in said environment of said assistance device.

4. A method as claimed in claim 1 wherein said assistance device comprises a locomotion unit configured to move an entirety of said assistance device, and comprising, in said computer, generating said interaction instruction to include a locomotion instruction and transferring said locomotion instruction to said locomotion unit and, via said locomotion unit, moving the entirety of said assistance device to execute a movement according to said locomotion instruction.

5. A method as claimed in claim 1 wherein said assistance device comprises a movable subsection that is movable relative to a further subsection of said assistance device, and comprising, in said computer, generating said interaction instruction to include a movement instruction and transferring said movement instruction to said movable subsection and changing a position of said movable subsection, with respect to said further subsection, dependent on said movement instruction.

6. A method as claimed in claim 1 wherein said input information comprises a voice input in a natural language, said voice input originating from at least one of said operator and said patient, and comprising, in said computing unit, processing said voice input using a natural language processing algorithm to generate said interaction instruction.

7. A method as claimed in claim 1 wherein said input interface is an optical interface configured to detect, as said input information, a human biomechanical movement selected from the group consisting of hand gestures, facial expressions and body movements, and comprising, in said computer, executing a pattern recognition algorithm to identify and interpret said biomechanical body movement to generate said interaction instruction dependent on said human biomechanical movement.

8. A method as claimed in claim 1 comprising, from said computer, storing said interaction instruction and the input information used to generate said interaction instruction as stored information data in a database accessible by said computer.

9. A method as claimed in claim 8 comprising acquiring subsequent information, after acquiring said input information, via said input interface and transferring the subsequent information from said input interface to said computer and, in said computer, processing said subsequent input information by retrieving said stored information data from said database and generating a subsequent interaction instruction based on said subsequent input information and the retrieved stored information data, and transferring the subsequent interaction instruction from said computer to said interaction interface, and performing a subsequent interaction involving said assistance recipient via said assistance device, dependent on said subsequent interaction instruction.

10. A method as claimed in claim 1 comprising, in said computer, generating said interaction instruction by producing a plurality of hypotheses for potential interaction instructions, evaluating said plurality of hypotheses to select at least one interaction instruction, as a selected interaction instruction, from said potential interaction instructions, and transferring said selected interaction instruction, as said generated interaction instruction, from said computer to said interaction interface.

11. A method as claimed in claim 10 comprising, via said assistance device, interacting with said assistance recipient according to said selected interaction instruction and also via said assistance device, emitting an output designating an associated rating for the hypothesis associated with said selected interaction instruction.

12. A method as claimed in claim 1 wherein said assistance device is a first assistance device among a plurality of assistance devices respectively assigned to a plurality of different medical apparatuses, and comprising, in said computer, generating respective interactive instructions individually designed for the respective assistance device that will interact with said assistance recipient.

13. A method as claimed in claim 1, comprising situating said assistance device in an examination room in which said assistance recipient is also situated and configuring said computer as an external computer and situating said external computer outside of said examination room.

14. An assistance system comprising:
an assistance device configured to interact with an assistance recipient, said assistance recipient being selected from the group consisting of a medical apparatus, an operator of a medical apparatus, and a patient receiving treatment or an examination from a medical apparatus, said assistance device being configured to execute a plurality of interactions involving said assistance recipient, each interaction providing assistance in a medical procedure;
said assistance device comprising an input interface that acquires input information, and said input information originating from said assistance recipient;
a computer;
said input interface being configured to transfer the acquired input information from the input interface to said computer;
said computer being configured to automatically process said input information to generate an interaction instruction dependent on said input information;
said assistance device comprising an interaction interface and said computer being configured to transfer the generated interaction instruction from the computer to the interaction interface of said assistance device;
said assistance device being configured to identify, from said interaction instruction, at least one interaction among said plurality of interactions and, via said interaction interface, and to perform said at least one interaction with said assistance recipient in said environment of said assistance device;
at least one database that is accessible by said computer, in which stored data are stored describing at least one of an examination of said patient conducted using said medical apparatus and a treatment of said patient conducted using said medical apparatus; and
said computer being configured to access said stored data from said at least one database and to process said input information to generate said interaction instruction dependent on the accessed stored data.

15. An assistance system as claimed in claim 14 wherein said interaction interface of said assistance device comprises an output interface, and wherein said computer is configured to generate output information as a part of said interaction instruction and to transfer said output information to said output interface, and wherein said output interface is configured to emit said output information to said assistance recipient.

16. An assistance system as claimed in claim 14 wherein said interaction interface of said assistance device comprises a gripper arm, and wherein said computer is configured to generate said interaction instruction to include a gripper arm operating instruction, and to transfer said gripper arm operating instruction to said interaction interface and wherein said gripper arm is configured to perform a physical interaction, dependent on said gripper arm operating instruction, with said assistance recipient in said environment of said assistance device.

17. An assistance system as claimed in claim 14 wherein said assistance device comprises a locomotion unit configured to move an entirety of said assistance device, and wherein said computer is configured to generate said interaction instruction to include a locomotion instruction and to transfer said locomotion instruction to said locomotion unit, and wherein said locomotion unit is configured to move the entirety of said assistance device to execute a movement according to said locomotion instruction.

18. An assistance system as claimed in claim 14 wherein said assistance device comprises a movable subsection that is movable relative to a further subsection of said assistance device, and wherein said computer is configured to generate said interaction instruction to include a movement instruction and to transfer said movement instruction to said movable subsection and wherein said movable subsection is configured to change a position of said movable subsection, with respect to said further subsection, dependent on said movement instruction.

19. An assistance system as claimed in claim 14 wherein input interface is configured to acquire said input information as a voice input in a natural language, said voice input originating from at least one of said operator and said patient, and wherein said computing unit is configured to process said voice input using a natural language processing algorithm to generate said interaction instruction.

20. An assistance system as claimed in claim 14 wherein said input interface is an optical interface configured to detect, as said input information, a human biomechanical movement selected from the group consisting of hand gestures, facial expressions and body movements, and wherein said computer is configured to execute a pattern recognition algorithm to identify and interpret said biomechanical body movement to generate said interaction instruction dependent on said human biomechanical movement.

21. An assistance system as claimed in claim 14 comprising a database accessible by said computer, and wherein said computer is configured to store said interaction instruction and the input information used to generate said interaction instruction as stored information data in said database.

22. An assistance system as claimed in claim 21 wherein said input interface is configured to acquire subsequent information, after acquiring said input information, and to transfer the subsequent information from said input interface to said computer, and wherein said computer is configured to process said subsequent input information by retrieving said stored information data from said database and to generate a subsequent interaction instruction based on said subsequent input information and the retrieved stored information data, and to transfer the subsequent interaction instruction from said computer to said interaction interface, and wherein said interaction interface is configured to perform a subsequent interaction involving said assistance recipient via said assistance device, dependent on said subsequent interaction instruction.

23. An assistance system as claimed in claim 14 wherein said computer is configured to generate said interaction instruction by producing a plurality of hypotheses for potential interaction instructions, and to evaluate said plurality of hypotheses to select at least one interaction instruction, as a selected interaction instruction, from said potential interaction instructions, and to transfer said selected interaction instruction, as said generated interaction instruction, from said computer to said interaction interface.

24. An assistance system as claimed in claim 23 wherein said assistance device is configured to interact with said assistance recipient according to said selected interaction instruction, and to emit an output designating an associated rating for the hypothesis associated with said selected interaction instruction.

25. An assistance system as claimed in claim 14 wherein said assistance device is a first assistance device among a plurality of assistance devices respectively assigned to a plurality of different medical apparatuses, and wherein said computer is configured to, generate respective interactive instructions individually designed for the respective assistance device that will interact with said assistance recipient.

26. An assistance system as claimed in claim 14 wherein said assistance device is a robot.

27. An assistance system as claimed in claim 26 wherein said robot is a humanoid robot.

* * * * *